United States Patent [19]

Goddard et al.

[11] Patent Number: 4,782,011
[45] Date of Patent: Nov. 1, 1988

[54] BISPHENOL DERIVATIVE STABILIZERS

[75] Inventors: John D. Goddard; Nigel E. Milner; Llewellyn J. Leyshon, all of Harrow, United Kingdom

[73] Assignee: Eastman Kodak Company, Rochester, N.Y.

[21] Appl. No.: 35,970

[22] Filed: Apr. 8, 1987

[30] Foreign Application Priority Data

Apr. 30, 1986 [GB] United Kingdom ............... 8610610

[51] Int. Cl.$^4$ .......................... G03C 1/34; G03C 7/26
[52] U.S. Cl. .................................... 430/551; 430/372
[58] Field of Search ............... 430/551, 372, 546, 552, 430/553

[56] References Cited

U.S. PATENT DOCUMENTS 4,207,393 6/1980 Snyder .
4,363,873 12/1982 Boon et al. .
4,594,314 6/1986 Kimura et al. ..................... 430/553
4,621,047 11/1986 Kishimoto et al. ................. 430/552

FOREIGN PATENT DOCUMENTS 1250641 11/1986 Japan .................... 430/551
2043641 2/1987 Japan .................... 430/551
1267287 3/1972 United Kingdom .

Primary Examiner—Paul R. Michl
Assistant Examiner—Lee C. Wright
Attorney, Agent, or Firm—Harold E. Cole

[57] ABSTRACT

A photographic element comprising a support having thereon at least one silver halide emulsion layer having associated therewith a dye-forming coupler and a dye stabilizer comprising a bisphenol derivative having two linked phenol rings, one of the phenolic hydroxy groups being substituted and at least one of the phenol rings being substituted.

In a preferred embodiment, the bisphenol derivative has the following formula:

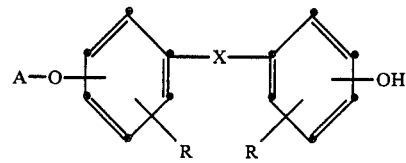

wherein
A is a substituted or unsubstituted alkyl, cycloalkyl, alkenyl, aryl, acyl, alkylsulfonyl or arylsulfonyl group;
X is a single bond or a linking group selected from alkylidene, a heteroatom or sulfonyl; and,
each R independently represents one or more substituents, each substituent independently being a substituted or unsubstituted alkyl, alkenyl, cycloalkyl or aryl group; or each R in combination with the benzene ring to which it is attached independently represents the atoms necessary to complete a fused ring system.

7 Claims, No Drawings

BISPHENOL DERIVATIVE STABILIZERS

This invention relates to the stabilization of dye images produced in photographic materials. More particularly, it relates to the use of certain bisphenol derivative stabilizers for improving the stability of dye images obtained by color developing coupler-incorporated photographic silver halide materials.

A common form of color photographic material comprises red-, green- and blue-sensitive silver halide emulsion layers in or adjacent to which are incorporated cyan-, magenta- and yellow-dye forming couplers, respectively. On development of such a material with a developer containing p-phenylenediamine color developing agent, the oxidation product produced on reduction of the silver halide by the developing agent reacts with the appropriate coupler to give image dye.

U.S. Pat. Nos. 4,363,873 and 4,207,393 relate to certain bisphenol compounds which are somewhat similar to the compounds used in this invention. The compounds used in these patents, however, are photographic contrast enhancers and are not taught to have any utility as stabilizers.

It is known to include stabilizers in color photographic materials in order to reduce the deterioration of the dye image which can occur in time as a result of the action of light, heat and/or humidity. British Pat. No. 1,267,287 describes the use of particular bisphenol derivatives to improve the light-keeping properties of color images formed by color development of light-sensitive silver halide color photographic materials. There is a problem associated with the use of those bisphenol derivatives, however, in that they cause hue contamination in the developed dye image.

The stabilizers employed in the present invention provide good light-keeping properties without the associated problem of hue contamination thereby allowing superior color rendition in the developed dye image.

The stabilizers employed in the present invention may also be used to protect photographic dye images from the deleterious action of heat and humidity and therefore may be used to improve the dark-keeping properties of photographic dye images.

These and other objects are achieved in accordance with the invention which comprises a photographic element comprising a support having thereon at least one silver halide emulsion layer having associated therewith a dye-forming coupler and a dye stabilizer comprising a bisphenol derivative having two linked phenol rings, one of the phenolic hydroxy groups being substituted and at least one of the phenol rings being substituted.

It is believed that as a result of one of the phenolic hydroxy groups being substituted or chemically blocked, the bisphenol derivatives provide superior color rendition of images, compared with their unblocked precursors, due to their lower propensity to react with oxidized developer, while retaining good activity as stabilizers. In addition, the blocked stabilizers may be incorporated into a color photographic system in high concentrations and with couplers of low activity without the danger of significant amounts of unwanted image dyes being formed by competitive reaction with oxidized developer.

The blocking group of the phenolic hydroxyl group of the bisphenol stabilizer of the invention may be any group which does not affect the desired properties of the stabilizer.

The two phenol rings of the stabilizer may be linked directly by a single bond or indirectly by a linking group. In a preferred embodiment of the invention, the link between the phenol rings is ortho relative to the phenolic hydroxy group of one ring and the blocked phenolic hydroxy group of the other ring.

In another preferred embodiment, each phenol ring independently is substituted in a position ortho or para relative to the unblocked or blocked phenolic hydroxy groups. It is further preferred that substituents are present in both ortho and para positions.

A preferred group of stabilizers is represented by the following general formula

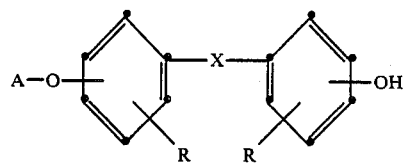

wherein

A is a blocking group such as a substituted or unsubstituted alkyl group, e.g., methyl, ethyl, propyl or butyl; a substituted or unsubstituted cycloalkyl group, e.g., cyclohexyl; a substituted or unsubstituted alkenyl group; a substituted or unsubstituted aryl group, e.g., phenyl; a substituted or unsubstituted acyl group, e.g., acetyl or benzoyl; or a substituted or unsubstituted alkylsulfonyl or arylsulfonyl group;

X is a single bond or a linking group such as alkylidene, e.g., butylidene or 3,5,5,-trimethylhexylidene; a heteroatom, e.g., oxygen or sulfur; or sulfonyl; and, each R independently represents one or more substituents, each substituent independently being a substituted or unsubstituted alkyl, alkenyl, cycloalkyl or aryl group; or each R in combination with the benzene ring to which it is attached independently represents the atoms necessary to complete a fused ring system. In a preferred embodiment of the invention, R is $CH_3$, $C_4H_9$-t or

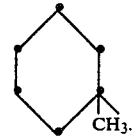

In another preferred embodiment of the invention, the stabilizers are represented by the general formula

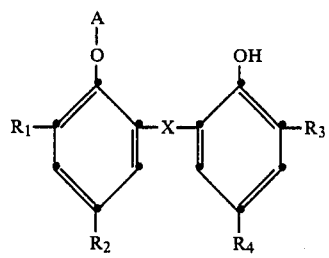

wherein

A and X are as defined above and, $R_1$, $R_2$, $R_3$ and $R_4$ each independently represents a substituted or unsubstituted alkyl, alkenyl, cycloalkyl or aryl group. In yet another preferred embodiment of the invention, $R_1$ and $R_3$ are identical and $R_2$ and $R_4$ are identical.

In still another preferred embodiment of the invention, X is S or $-(CR_5R_6)_n-$, each $R_5$ and $R_6$ independently being hydrogen or a substituted or unsubstituted alkyl, cycloalkyl, alkenyl or aryl group and n is an integer of from 1 to about 10.

In still another preferred embodiment of the invention, A is $CH_2C_6H_5$, $C_4H_9$, $COCH_3$, $C_2H_5$, $COC_6H_5$, $OC-CH=CH_2$, $OCCH_2CH_3$,

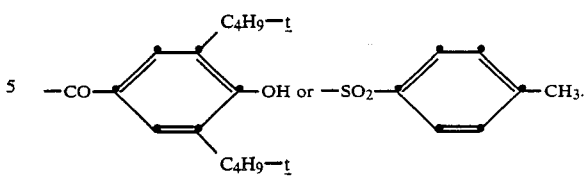

Specific examples of stabilizers suitable for use in the present invention are as follows:

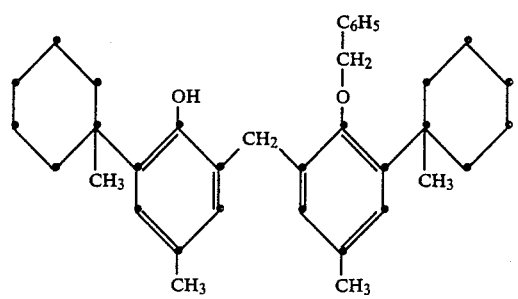
(1)

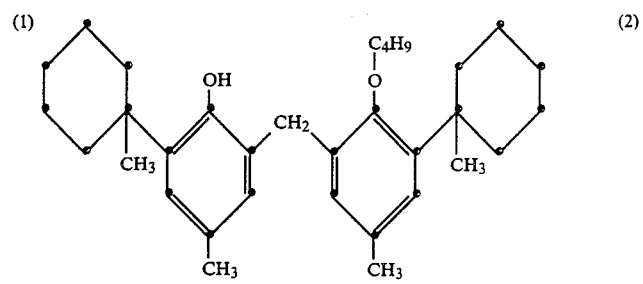
(2)

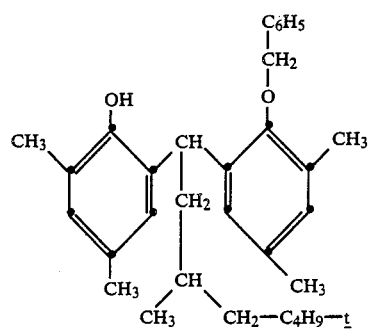
(3)

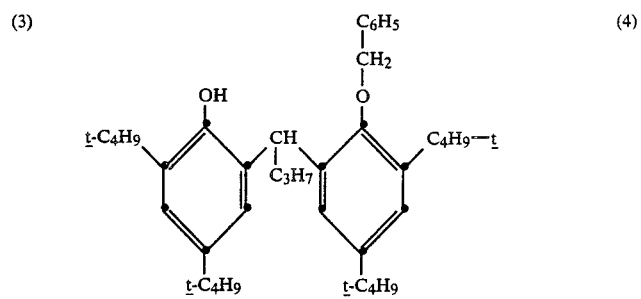
(4)

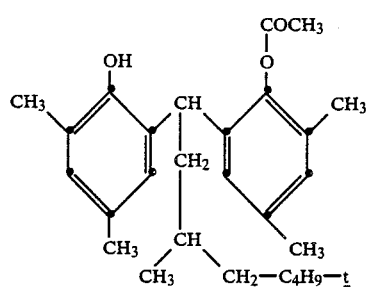
(5)

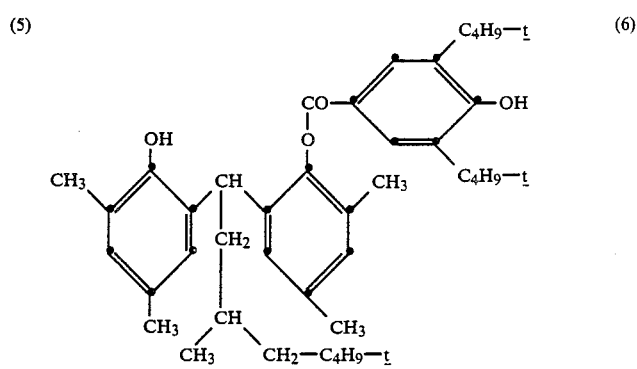
(6)

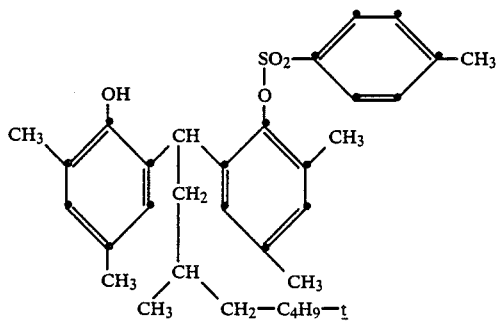
(7)

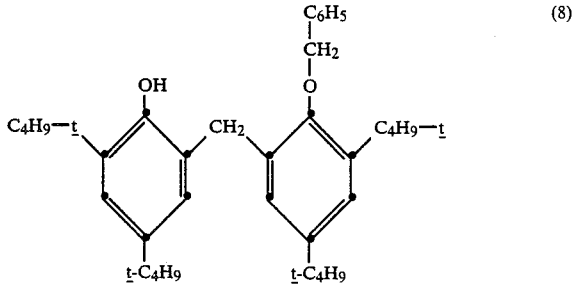
(8)

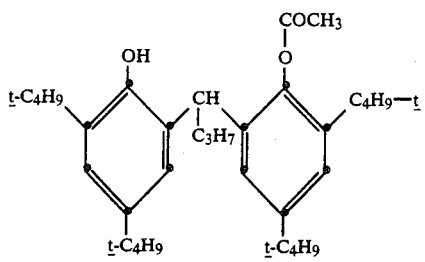 (5)

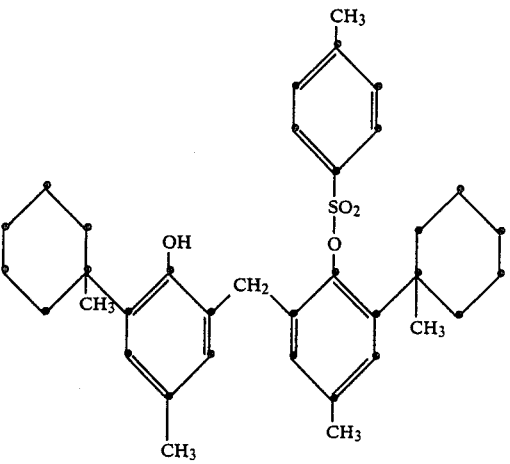 (10)

-continued (9)

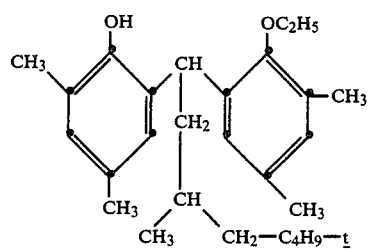 (11)

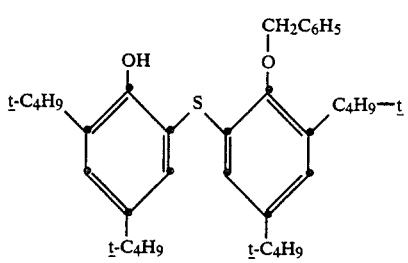 (12)

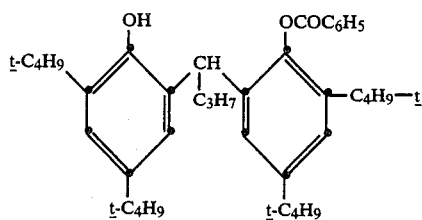 (13)

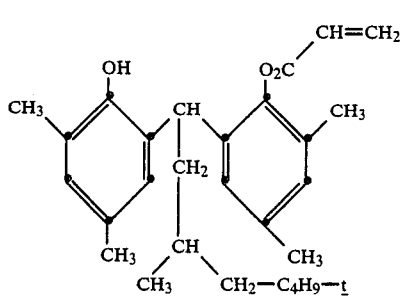 (14)

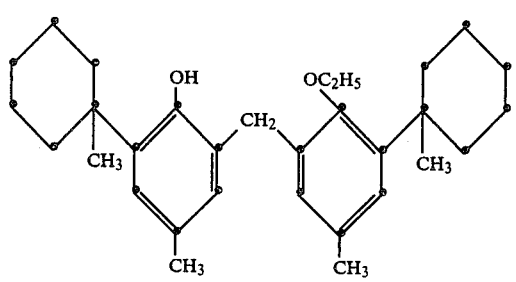 (15)

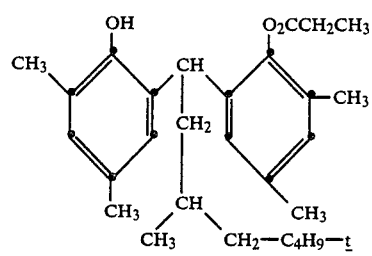 (16)

The blocked bisphenol derivatives are readily prepared from their unblocked counterparts, many of which are commercially available. For example, a blocking group may be introduced into the unblocked parent bisphenol by reaction with an appropriate reactive halogen containing compound e.g., an alkyl bromide, acyl chloride, sulfonyl chloride or a dialkyl sulfate e.g., diethyl sulfate.

Examples of unblocked parent bisphenols from which the stabilizers used in the present invention may be prepared are as follows:

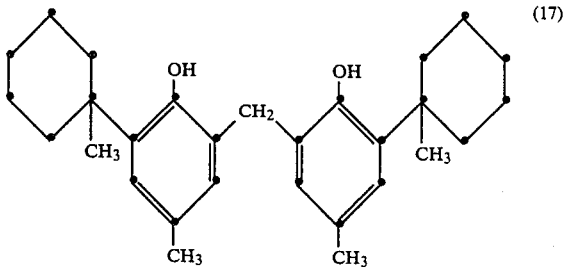 (17)

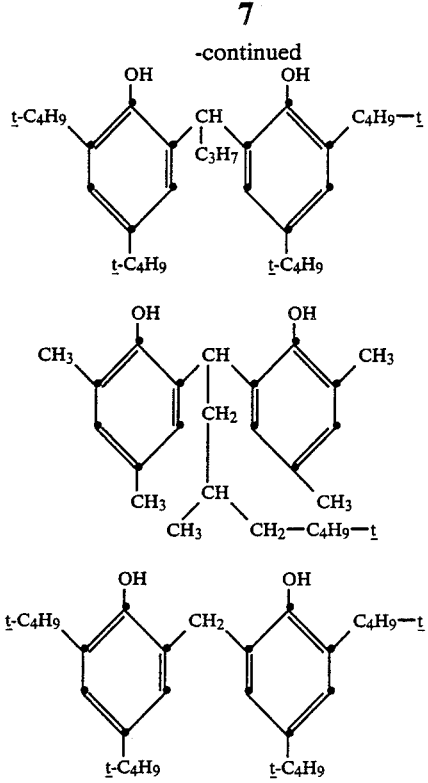

The blocked bisphenol derivatives are used in an amount sufficient to stabilize the photographic image dyes and their precursors e.g., in an amount from about 0.2 to about 2.0 mole per mole coupler, more preferably from about 0.5 to about 1.0 mole per mole coupler.

Because the blocked bisphenol derivative is used as a dye stabilizer, it must be incorporated in the silver halide emulsion layer or a layer adjacent thereto. It can be incorporated as a separate dispersion, but is preferably incorporated in admixture with the coupler. Both coupler and stabilizer may be dissolved in a conventional coupler solvent, such as dibutyl phthalate. As in the production of ordinary coupler dispersions, a volatile and/or water-miscible auxiliary solvent, such as ethyl acetate, may be used to aid the dispersion process and then removed by evaporation or by washing the set dispersion. Also, the dispersion process can be assisted by the presence of a surface active compound, as usual in the manufacture of coupler dispersions.

In the following discussion of suitable materials for use in the emulsions and elements of this invention, reference will be made to Research Disclosure, December 1978, Item 17643, published by Industrial Opportunities Ltd., The Old Harbourmaster's, 8 North Street, Emsworth, Hants P010 7DD, U.K., the disclosures of which are incorporated herein by reference. This publication will be identified hereafter as "Research Disclosure". References giving information on couplers and on methods for their dispersions are given in Sections VII and XIV, respectively, of Research Disclosure.

The couplers commonly employed in photographic materials are water-insoluble compounds often containing ballast groups, phenolic (including naphtholic) couplers being used for producing cyan dyes and compounds containing an activated methylene group, including both heterocyclic and open-chain compounds, being used for producing magenta and yellow dyes. Important magenta couplers are pyrazolones and important yellow couplers are benzoylacetanilides. Patents describing couplers include the following U.S. Pat. Nos.:

Cyan dye-forming
3,367,531
3,034,892
2,423,730
3,311,476
2,474,293
3,419,390
2,772,826
3,458,315
2,895,826
3,476,563

Magenta Dye forming
2,343,703
3,062,653
2,369,489
3,127,269
2,600,788
3,311,476
2,908,573
3,419,391
2,933,391
3,518,429

Yellow dye-forming
2,298,443
3,277,155
2,407,210
3,408,194
2,875,057
3,415,652
2,908,573
3,447,928
3,265,506
3,933,501

An account of dye-forming development is given in 'Modern Photographic Processing', Vol. 2, Grant Haist, Wiley, New York, 1978, Chapter 9.

The stabilizers are useful in any coupler-incorporated silver halide photographic materials, including monochrome materials, false-color materials and color transparency, negative and print materials, to stabilize the image dye obtained on development with a solution including a p-phenylenediamine color developing agent. Such developing agents are well-known, being described in, for example *Photographic Processing Chemistry*, L. F. A. Mason, Focal Press, London, 2nd edition (1975) pp 229–235 and *Modern Photographic Processing*, Grant Haist, Wiley, New York (1979), Volume 2 pp 463–8.

The silver halide emulsion employed in the elements of this invention can be either negative-working or positive-working. Suitable emulsions and their preparation are described in Research Disclosure Sections I and II and the publications cited therein. Suitable vehicles for the emulsion layers and other layers of elements of this invention are described in Research Disclosure Section IX and the publications cited therein.

The photographic elements of this invention or individual layers thereof, can contain brighteners (see Research Disclosure Section V), antifoggants and stabilizers (see Research Disclosure Section VI), antistain agents and image dye stabilizer (see Research Disclosure Section VII, paragraphs I and J), light absorbing and scattering materials (see Research Disclosure Section VIII), hardeners (see Research Disclosure Section XI), plasticizers and lubricants (see Research Disclosure Section XII), antistatic agents (see Research Disclosure Section XIII), matting agents (see Research Disclosure Section XVI) and development modifiers (see Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide emulsions this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Examples of the preparation of stabilizer compounds used in the present invention are as follows:

PREPARATIVE EXAMPLE 1

Preparation of 2-(3,5-di-tert-butyl-2-hydroxyphenylbutylidene)-4,6-di-tert-butylphenylbenzoate (Compound 13)

To a stirred mixture of anhydrous calcium chloride (75 g), butyraldehyde (36.1 g, 0.5 mole) and 2,4-di-tert-butylphenol (206.3 g, 1.0 mole) at 70° C. was added, dropwise, concentrated hydrochloric acid (45 ml). The reaction mixture was stirred at this temperature for 12 hours. The resulting solid, 2,2'-butylidene bis(4,6-di-tert-butylphenol) (Compound 18), was washed with water, dried under vacuum and recrystallized from heptane. Yield=51% M.p. 113°–114° C.

A solution of 2,2'-butylidenebis(4,6-di-tert-butylphenol) (37.4 g, 0.08 mole) and triethylamine (8.1 g, 0.08 mole) in dry tetrahydrofuran (250 ml) was treated dropwise under stirring with a solution of benzoyl chloride (12.5 g, 0.088 mole) in dry tetrahydrofuran (30 ml). The reaction mixture was stirred overnight, evaporated to dryness under vacuum and the residue redissolved in ethyl acetate. The organic layer was washed with dilute hydrochloric acid, water and then dried (MgSO$_4$). The solvent was removed under vacuum and the residue recrystallized from ethyl acetate. Yield=40% M.p. 180°–182° C.

PREPARATIVE EXAMPLE 2

Preparation of 2-[1-(2-benzyloxy-3,5-dimethylphenyl)-3,5,5-trimethylhexylidene]-4,6-dimethylphenol (Compound 3)

A solution of 2,2'-(3,5,5-trimethylhexylidene)-bis(4,6-dimethylphenol) (184.0 g, 0.5 mole) in acetone (2l) was stirred with anhydrous potassium carbonate (170 g) and benzylbromide (85.5 g, 0.5 mole) at room temperature overnight. The solution was filtered, excess acetone removed under vacuum and the residue refrigerated. The crystalline solid was filtered off, washed with cold acetone and dried under vacuum at 40° C. Yield=66%. M.p.=125°–126° C.

PREPARATIVE EXAMPLE 3

Preparation of 2-[1-(2-benzyloxy-3-(1-methylcyclohexyl)-5-methylphenyl)methylene]-4-methyl-6-(1-methylcyclohexyl)-phenol (Compound 1)

2,2'-Methylenebis-4-methyl-6-(1-methylcyclohexyl)-phenol (168.0 g, 0.4 mole) in acetone (200 ml) was stirred overnight at room temperature with anhydrous potassium carbonate (80 g) and benzyl bromide (68.4 g, 0.4 mole). The potassium carbonate was filtered off and the filtrate poured into water with stirring. The aqueous layer was poured off the gummy solid and crystallization was induced by stirring with methanol. The solid was filtered off, dried, ground up and slurried with methanol to effect final purification. Yield=77%, M.p. 97°–99° C.

In order to confirm that unblocked bisphenol stabilizer compounds can behave as color couplers so that image hue contamination is produced, the following experiment was performed.

A solution of Compound 18 in ethyl acetate was shaken in a test tube with an aqueous solution of sodium carbonate and the color developing agent 4-N-ethyl-N-(β-methanesulphonamidoethyl)amino-o-toluidine to which was added a small amount of potassium persulfate. A deep green color slowly developed in the ethyl acetate layer. In the absence of the color developing agent no color was generated. In a control experiment using all components except Compound 18 only a weak blue-green coloration was produced. When the experiment was repeated replacing Compound 18 with Compound 4 or Compound 9 (two blocked derivatives of Compound 18), the results were indistinguishable from the control experiment. It may thus be concluded that Compound 18 reacts with oxidized developer to form a green dye, whereas its two blocked derivatives Compounds 4 and 9 are unreactive.

In another experiment, methanolic solutions of Compounds 17 and 19 were spotted onto a thin layer chromatography (TLC) plate, chromatographed and successively sprayed with a solution of the aforementioned color developing agent in methanol and an aqueous solution of sodium carbonate and potassium persulfate. A brown spot developed with Compound 17 and a green spot was generated by Compound 19. Omission of the color developing agent spray prevented color formation thereby demonstrating the existence of a reaction between the unblocked bisphenols and the color developing agent.

The invention is further described in the following photographic examples.

EXAMPLE 1

Two coatings were prepared from different dispersions of coupler C-1.

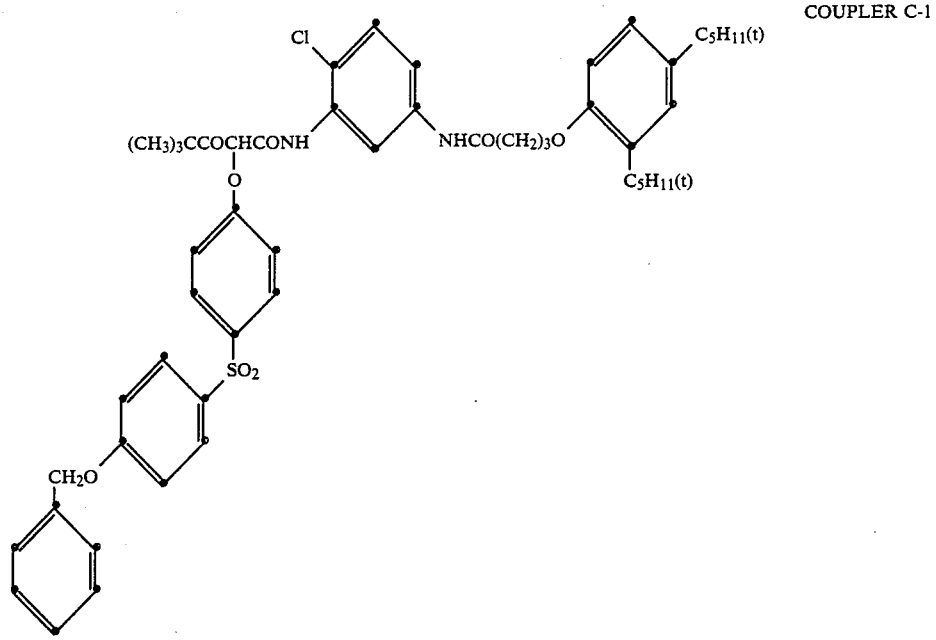

COUPLER C-1

For the first dispersion, coupler C-1 was dissolved in an equal weight of ethyl acetate and 1.5 mole-equivalents (based on coupler C-1) dibutyl phthalate added. This solution was ultrasonically dispersed with a 12.5% by weight gelatin solution containing about 1% by weight of an alkyl naphthalene sulfonate surfactant (Nekal ® available from BASF). The second dispersion was prepared in an identical fashion except that Compound 1 was added to the coupler solution at a rate of 0.5 mole per mole coupler C-1. Both dispersions were coated with a silver chlorobromide emulsion on a resin coated paper support to give coverages of 0.344 g/m² Ag, 1.36 g/m² gelatin and 0.83 mmole/m² coupler C-1. The emulsion layers were overcoated with a gelatin layer at a coverage of 3.0 g/m² containing 0.065 g/m² bisvinylsulfonylmethyl ether.

Sample strips of the two coatings were exposed through a graduated density test object and processed through a standard Ektaprint-2 process (see British Journal of Photography Annual 1986, pages 37 and 38) with an acid stop-bath included between development and bleach-fix. Examination of the processed strips showed that the coating containing Compound 1 exhibited no degradation of the yellow image dye hue.

The processed strips were faded with light from a Xenon source (luminant intensity 5.4 Klux at the sample plane) filtered through a U.V. light absorbing layer consisting of a coating of Tinuvin 328 ® (available from Ciba Geigy) at 0.75 g/m² in gelatin. Sensitometric curves were measured (Status A blue filtration) from the strips of each coating before and after fading. The point on each curve corresponding to an initial density of 1.7 was chosen as a reference point. After four weeks fade, the density of the control coating had decreased by 0.1 density units from this point. The presence of Compound 1 reduced this density loss to 0.06 density units which indicates a significant improvement in dye stability.

For comparison, two coatings of coupler C-1 with and without Compound 17 were prepared and treated in the manner indicated above. Examination of the processed strips showed that the coating containing Compound 17 exhibited a less pure yellow hue, attributable to the production of a second dye from the reaction of oxidized developer with the stabilizer. The extent of the hue contamination was quantified by comparing Status A red and blue reflection densities from the two coatings. For a blue density of 2.0 the corresponding red density of the coating containing Compound 17 was 0.12 compared with a value of 0.10 for the control coating containing only coupler C-1.

In the fade test, after eight weeks exposure the control coating had lost 0.40 density units from an initial blue reflection density of 1.7. The presence of Compound 17 reduced the density loss to 0.18 density units.

EXAMPLES 2 TO 5

A number of blocked bisphenol stabilizers were compared with the corresponding unblocked stabilizers.

Coatings of the blocked and unblocked stabilizers co-dispersed with coupler C-1 were prepared following the procedure of Example 1. A control coating of a dispersion of Coupler C-1 without any stabilizer was also prepared.

Sample strips of the coatings were exposed and developed as described in Example 1.

A quantitative estimate of the degree of color contamination in the various coatings was made by measuring the red absorption displayed by each strip at a given blue density. Table 1 shows the results obtained at a blue density of 2.0.

TABLE 1

| Example | Stabilizer | Status A Density Blue | Red |
|---|---|---|---|
| Control | None | 2.0 | 0.11 |
| 2 | 4 | 2.0 | 0.12 |
| 3 | 9 | 2.0 | 0.11 |
| Comparative | 18 | 2.0 | 0.14 |
| 4 | 6 | 2.0 | 0.10 |
| Comparative | 19 | 2.0 | 0.27 |
| 5 | 8 | 2.0 | 0.12 |

TABLE 1-continued

| Example | Stabilizer | Status A Density Blue | Red |
|---|---|---|---|
| Comparative | 20 | 2.0 | 0.17 |

The yellow image dye from coupler C-1 was generated in all the coatings but in the strips containing the unblocked stabilizers 18, 19 and 20 the hue of the dye was less pure than in the remaining strips. The coatings containing blocked stabilizers 4, 9, 6 and 8 were visually identical with the control coating.

Sample strips of the exposed and developed coatings described above were faded for various periods of time in accordance with the procedure described in Example 1. The results are shown in Table 2 wherein the figures appearing in the column headed Fade represent the loss in Status A blue reflection density from an initial value of 1.7. Such loss indicates the stability of the yellow image dye produced from coupler C-1 i.e., an increase in the loss of density means a decrease in dye stability.

TABLE 2

| Example | Stabilizer | Fade Time (weeks) | Fade (dens. units) |
|---|---|---|---|
| Control | None | 12 | −0.29 |
| 2 | 4 | 12 | −0.22 |
| 3 | 9 | 12 | −0.15 |
| Comparative | 18 | 12 | −0.21 |
| Control | None | 8 | −0.40 |
| 4 | 6 | 8 | −0.13 |
| Comparative | 19 | 8 | −0.14 |
| Control | None | 12 | −0.29 |
| 5 | 8 | 12 | −0.22 |
| Comparative | 20 | 12 | −0.20 |

The results show that all of the blocked stabilizers improve the stability of the yellow image dye and each one compares well with its unblocked parent in terms of stabilization efficiency.

EXAMPLE 6

Following the procedure described in Example 1, Compound 7 was co-dispersed with coupler C-2 and coated with a silver chloro-bromide photographic emulsion. Coupler C-2 has the structural formula:

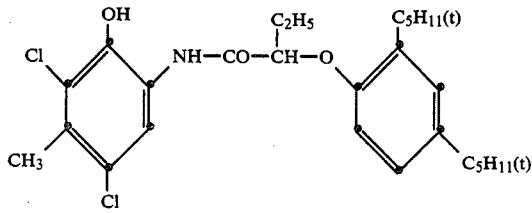

Component quantities were adjusted so that the final coating contained 1.34 mmole/m² coupler C-2, 1.34 mmole/m² Compound 7, 0.331 g/m² dibutylphthalate and 0.269 g/m² silver. A control coating was also prepared containing the same components with the exception of Compound 7.

Both coatings were exposed and developed in accordance with the procedure set forth in Example 1. In a wet incubation test, strips of each coating were hung for three weeks in a humidity cabinet maintained at 60° C. and 70% relative humidity. In a dry incubation test, strips of each coating were hung in a dry cabinet at 70° C. for three weeks.

Sensitometry was measured before and after incubation. The initial Status A red density of the strips before incubation was 1.7. The loss in status A red density following incubation was measured and the results are reported in Table 3 below.

TABLE 3

| Example | Status A Red Density Loss Wet Incubation | Dry Incubation |
|---|---|---|
| Control | −0.26 | −0.65 |
| 6 | −0.08 | −0.39 |

The data in Table 3 show that the presence of Compound 7 dramatically decreased the loss of cyan dye density under both incubation conditions.

EXAMPLES 7 AND 8

Following the procedure described in Example 1, Compounds 1 and 3 were co-dispersed with coupler C-3 and coated with a silver chlorobromide photographic emulsion. Coupler C-3 has the structural formula:

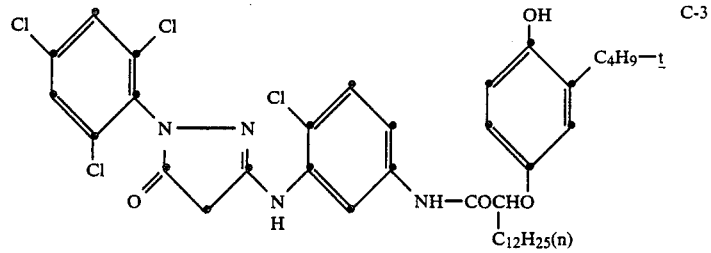

Component quantities were adjusted so that the final coatings contained 0.58 mmole/m² coupler C-3, 0.58 mmole/m² Compound 1 or 3, 0.226 g/m² dibutylphthalate and 0.474 g/m² silver. A control coating was also prepared containing the same components with the exception of Compounds 1 and 3.

The coatings were exposed, developed and subjected to a light fade test in accordance with the procedure set forth in Example 1.

Sensitometry was measured before and after fading. Following fading, the loss in status A green density from an initial value of 1.7 was measured and the results are reported in Table 4 below.

TABLE 4

| Example | Stabilizer | Fade Time (weeks) | Fade (dens. units) |
|---|---|---|---|
| Control | None | 6 | −0.20 |
| 7 | 1 | 6 | −0.15 |
| 8 | 3 | 6 | −0.17 |

The data in Table 4 shows that the presence of Compounds 1 and 3 decreased the loss of magenta dye density under the fading conditions.

The invention has been described in detail with particular reference to preferred embodiments thereof, but it will be understood that variations and modifications can be effected within the spirit and scope of the invention.

What is claimed is:

1. A photographic element comprising a support having thereon at least one silver halide emulsion layer having associated therewith a dye-forming coupler and a dye stabilizer comprising a bisphenol derivative having the following formula:

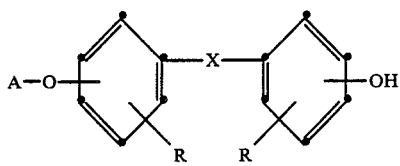

wherein

A is a substituted or unsubstituted alkyl, cycloalkyl, alkenyl, aryl, acyl, alkylsulfonyl or arylsulfonyl group;

X is a single bond or a linking group selected from alkylidene, a heteroatom or sulfonyl; and, each R independently represents one or more substituents, each substituent independently being a substituted or unsubstituted alkyl, alkenyl, cycloalkyl or aryl group; or each R in combination with the benzene ring to which it is attached independently represents the atoms necessary to complete a fused ring system.

2. The element of claim 1 wherein the bisphenol derivative has the formula:

wherein

A and X are as defined in claim 1; and $R_1$, $R_2$, $R_3$ and $R_4$ each independently represents a substituted or unsubstituted alkyl, alkenyl, cycloalkyl or aryl group.

3. The element of claim 2 wherein $R_1$ and $R_3$ are identical and $R_2$ and $R_4$ are identical.

4. The element of claim 2 wherein X is S or $-(CR_5R_6)_n-$, each $R_5$ and $R_6$ independently being hydrogen or a substituted or unsubstituted alkyl, cycloalkyl, alkenyl or aryl group and n is an integer of from 1 to about 10.

5. The element of claim 2 wherein the bisphenol derivative is present in an amount of from about 0.2 to about 2.0 moles per mole of coupler.

6. The element of claim 1 wherein R is $CH_3$, $C_4H_9$-t or

7. The element of claim 2 wherein A is $CH_2C_6H_5$, $C_4H_9$, $COCH_3$, $C_2H_5$, $COC_6H_5$, $OC-CH=CH_2$, $OCCH_2CH_3$, $-CO-$⟨ring with $C_4H_9-t$, $C_4H_9-t$⟩$-OH$ or $-SO_2-$⟨ring⟩$-CH_3$.

* * * * *